(12) United States Patent
Miserlis et al.

(10) Patent No.: US 10,456,063 B2
(45) Date of Patent: *Oct. 29, 2019

(54) SYSTEM AND METHOD FOR MONITORING PLEURAL FLUID

(71) Applicant: Board of Regents of the University of Nebraska, Lincoln, NE (US)

(72) Inventors: Dimitrios Miserlis, Omaha, NE (US); Kim Cluff, Andover, KS (US); Abby M. Kelly, Lincoln, NE (US); Suzanne J. Higgins, Lincoln, NE (US); Max H. Twedt, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/861,362

(22) Filed: Jan. 3, 2018

(65) Prior Publication Data

US 2018/0125398 A1 May 10, 2018

Related U.S. Application Data

(63) Continuation of application No. 14/378,670, filed as application No. PCT/US2013/026362 on Feb. 15, 2013, now Pat. No. 9,888,870.

(Continued)

(51) Int. Cl.
*A61B 5/145* (2006.01)
*A61B 5/08* (2006.01)
(Continued)

(52) U.S. Cl.
CPC ............ *A61B 5/14507* (2013.01); *A61B 5/08* (2013.01); *A61B 5/0813* (2013.01);
(Continued)

(58) Field of Classification Search
CPC ............ A61M 1/0025; A61M 16/0003; A61M 2039/0267; A61M 2210/101;
(Continued)

(56) References Cited

U.S. PATENT DOCUMENTS 4,654,029 A 3/1987 D'Antonio
5,149,325 A 9/1992 Telang et al.
(Continued)

FOREIGN PATENT DOCUMENTS

WO 2009105432 A2 8/2009
WO 2017155994 A1 9/2017

OTHER PUBLICATIONS

Extended European Search Report issued in EP13748608.0 dated Sep. 16, 2015.
(Continued)

*Primary Examiner* — Eric F Winakur
(74) *Attorney, Agent, or Firm* — The Webb Law Firm

(57) ABSTRACT

The disclosure is directed to intrapleural air leak detection and monitoring. According to various embodiments of the disclosure, an air leak may be detected utilizing at least one sensor to determine whether fluid extracted from a pleural cavity of a patient includes carbon dioxide and/or a second substance. The second substance may be a foreign substance inhaled by the patient to confirm presence of the air leak. The air leak may be further monitored over a period of time by collecting temporally successive measurements associated with detected concentrations of carbon dioxide. Therefore, tissue damage and recovery may be assessed according to objectively collected criteria.

19 Claims, 7 Drawing Sheets

Related U.S. Application Data

(60) Provisional application No. 61/599,724, filed on Feb. 16, 2012.

(51) Int. Cl.
*A61M 1/00* (2006.01)
*A61B 5/091* (2006.01)

(52) U.S. Cl.
CPC ........... *A61M 1/0025* (2014.02); *A61B 5/091* (2013.01); *A61M 2202/025* (2013.01); *A61M 2202/0225* (2013.01); *A61M 2202/0275* (2013.01); *A61M 2210/101* (2013.01)

(58) Field of Classification Search
CPC .... A61M 2202/025; A61M 2202/0275; A61B 5/08; A61B 5/0813; A61B 5/14507
See application file for complete search history.

(56) References Cited

U.S. PATENT DOCUMENTS

| | | |
|---|---|---|
| 6,983,750 B2 | 1/2006 | Heinonen |
| 2006/0025650 A1 | 2/2006 | Gavriely |
| 2009/0118646 A1 | 5/2009 | Svanberg et al. |
| 2010/0130947 A1 | 5/2010 | Daly |
| 2011/0054340 A1* | 3/2011 | Russ ...................... A61M 1/04 600/529 |
| 2011/0071415 A1 | 3/2011 | Karwoski et al. |
| 2011/0087122 A1 | 4/2011 | Aljuri et al. |
| 2011/0201956 A1 | 8/2011 | Alferness et al. |
| 2013/0110057 A1 | 5/2013 | Croteau et al. |
| 2013/0165877 A1 | 6/2013 | Leeson et al. |
| 2018/0104391 A1 | 4/2018 | Luxon et al. |

OTHER PUBLICATIONS

ISR/WO issued in PCT/US2013/026362 dated May 29, 2013.
IPRP issued in PCT/US2013/026362 dated Aug. 28, 2014.
Office Action issued in EP13748608.0 dated Sep. 1, 2016.
Office Action issued in U.S. Appl. No. 14/378,670 dated Sep. 14, 2016.
Office Action issued in U.S. Appl. No. 14/378,670 dated Apr. 5, 2017.
Office Action issued in EP 13748608.0 dated Dec. 19, 2017.
Office Action issued in EP 13748608.0 dated Sep. 11, 2018.

* cited by examiner

SYSTEM AND METHOD FOR MONITORING PLEURAL FLUID

PRIORITY

The present application is a continuation of U.S. patent application Ser. No. 14/378,670, now U.S. Pat. No. 9,888,870, entitled SYSTEM AND METHOD FOR MONITORING PLEURAL FLUID filed on Aug. 14, 2014, which is the national stage application of PCT/US13/26362 filed on Feb. 15, 2013, which claims priority to U.S. Provisional Application Ser. No. 61/599,724, entitled CHEST DRAINAGE SYSTEM FOR DIAGNOSIS AND QUANTIFICATION OF INTRAPLEURAL AIRLEAKS, by Dimitrios Miserlis et al., filed Feb. 16, 2012, which an application of which the current application is entitled to the benefit of its priority date. The above-identified patent applications are incorporated herein by reference for all they disclose.

TECHNICAL FIELD

The present disclosure generally relates to the field of pleural monitoring and more particularly to detection and quantification of intrapleural air leaks.

BACKGROUND

Penetration into a patient's pleura or lung parenchyma often results in air leaking into the pleural cavity, referred to as "pneumothorax". In addition to chest injury, disruption of the sealed pleural and thoracic space may also result from thoracic surgery. Increased intrapleural pressure from air leakage can cause a lung to collapse. Accordingly, a chest tube is often inserted in the pleural cavity to drain fluid and restore negative pressure in the intrapleural space of patients that have undergone lung surgery, surgery of adjacent organs, or suffered injury to lung tissue as a result of any type of chest trauma.

One method of chest drainage involves a chest tube fluidically coupled to a drainage canister. In some embodiments, the drainage canister includes a "3-bottle set-up", such as the PLEUR-EVAC system produced by TELEFLEX INCORPORATED or the OCEAN WET SUCTION WATER SEAL DRAIN produced by ATRIUM MAQUET GETINGE GROUP. The three bottles may include a collection bottle, a water-seal bottle, and a suction-control bottle. Suction is applied to the pleural cavity to withdraw fluid, including air "Pneumothorax" from an air leak and liquid "Hemothorax". Any gas withdrawn from the pleural cavity enters the collection bottle and passes into the water-seal bottle where it bubbles through water. The water in the water-seal bottle acts as a one-way valve preventing back flow of gas into the chest cavity. Clinicians typically detect air leaks by visually observing bubbles within the water-seal bottle. However, any detection, measurement, or grading of an air leak is prone to inconsistency caused by observer subjectivity and human error. The anatomy and physiology of the pleural space and the chest wall can lead to false positive detection of air leaks with current clinical methods (e.g. visual observation of bubbles and chest x-rays). Retained air within the pleural space may change position because of pleural space tissue movements, even when the bronchial and parenchymal leak site has been healed. Movement of retained air results in a delay in the removal of the chest tube and a subsequent increase in the morbidity rate, possible complications, patient discomfort, and unnecessary extension of hospital stay. Additionally, false negative detection of an air leak may occur when small leaks are concealed by collapsing tissues.

Air leaks are one of the most common complications after trauma in the thoracic space, as well as an expected medical problem after thoracic surgery. Air leaks are a common cause of prolonged hospitalization, adding significantly to the cost of medical care. See Cerfolio R J, Bass C S, Pask A H and Katholi C R. Predictors and treatment of persistent air leaks. Ann Thorac Surg 2002; 73: 1727-1730. Furthermore, patient recovery is difficult to assess with the currently employed detection and monitoring techniques (e.g. visual observation of bubbles and chest x-rays). Currently, it is customary to establish negative pressure suction for a specified time following a following a traumatic chest injury and/or thoracic surgery. This decision is done empirically and results in the inability to objectively monitor and customize treatment according to the healing/sealing process of the bronchial tree and lung parenchyma.

SUMMARY

The present disclosure is directed to a system and method for objectively detecting and monitoring an intrapleural air leak. By utilizing hard results and quantitative measurements, clinicians are enabled to diagnose patients and assess recovery with a higher degree of consistency. Accordingly, there is less chance that patients will be hospitalized beyond the actual recovery time or require emergent reinsertion of chest tube and readmission due to premature removal.

According to various embodiments, the system includes at least one detection unit configured to receive fluid from a pleural cavity of a patient. In some embodiments, the fluid includes air or another inhaled substance extracted from the pleural cavity utilizing a chest tube fluidically coupled to a drainage canister. The detection unit may include a sensor configured to detect carbon dioxide present in the fluid. The detection unit may further include a sensor configured to detect a second substance present in the fluid. The system further includes at least one processing unit in communication with the detection unit. The processing unit may be configured to provide a first electrical signal when carbon dioxide is detected in the fluid. The processing unit may be further configured to provide a second electrical signal when the second substance is detected in the fluid.

In some embodiments, the system further includes a user interface in communication with the processing unit. The user interface may be configured to provide an indication that carbon dioxide has been detected when the first signal is received from the processing unit. The user interface may be further configured to provide an indication that the second substance has been detected when the second signal is received from the at least one processing unit. In some embodiments, the second substance is a non-toxically inhaled substance that is foreign to the human body, such as helium, sulfur hexafluoride, or nitric oxide. Accordingly, detection of the second substance may confirm the presence of an air leak.

A method of detecting and monitoring intrapleural air leaks may be manifested by an embodiment of the system described herein. The method may include the steps of: receiving fluid from a pleural cavity of a patient; detecting carbon dioxide present in the fluid; providing a first indication when carbon dioxide is detected in the fluid; detecting a second substance present in the fluid; and providing a second indication when the second substance is detected in the fluid. In some embodiments, the concentration of carbon dioxide is detected and monitored over a period of time to quantify an air leak (i.e. tissue damage) and assess patient recovery (i.e. tissue healing).

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

Figure 1:
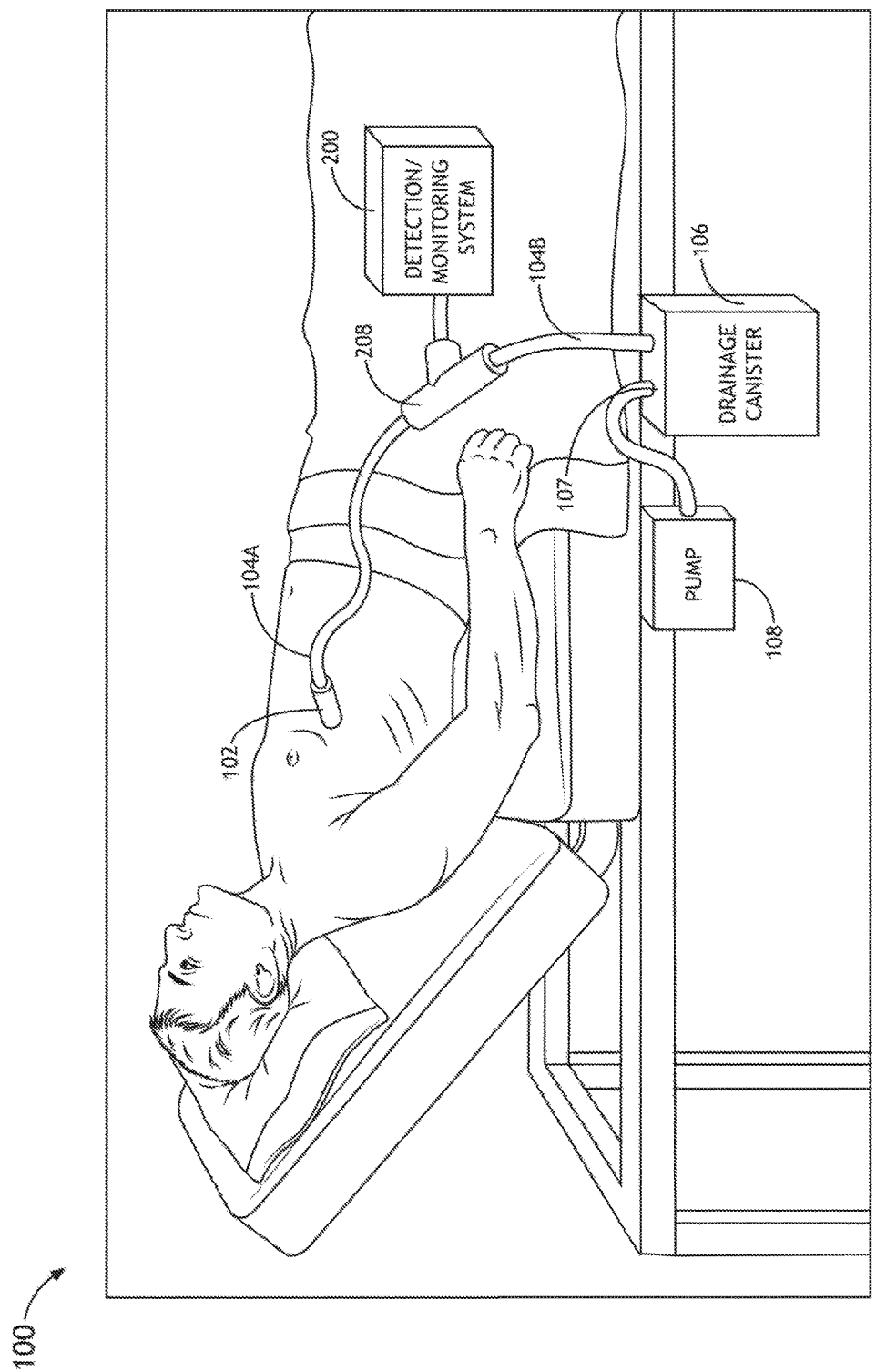
FIG. 1 illustrates a system for extracting fluid from a pleural cavity of a patient, in accordance with an embodiment of this disclosure.

The pleural cavity maintains pressure that is negative to the atmosphere, which keeps lungs pressed against the chest wall to prevent collapse of a lung during exhalation. The lung may collapse if negative pressure of the intrapleural space is lost or disrupted due to an air leak caused by surgery or any other type of trauma affecting the tissue. FIG. 1 illustrates a system 100 for restoring negative pressure by extracting fluid from the pleural cavity. In some embodiments, the system 100 includes a chest tube 102 configured to channel extracted fluid through a conduit 104 to a fluidically coupled drainage canister 106. The system 100 may further include a pump 108 (e.g. pneumatic or peristaltic pump) for suctioning the fluid through the chest tube 102. Many chest drainage systems are known to the art including, but not limited to, the PLEUR-EVAC system produced by TELEFLEX INCORPORATED or the OCEAN WET SUCTION WATER SEAL DRAIN produced by ATRIUM MAQUET GETINGE GROUP. Accordingly, the foregoing description of system 100 is included for illustrative purposes and is not intended to limit the present disclosure in any way.

Figure 2A:
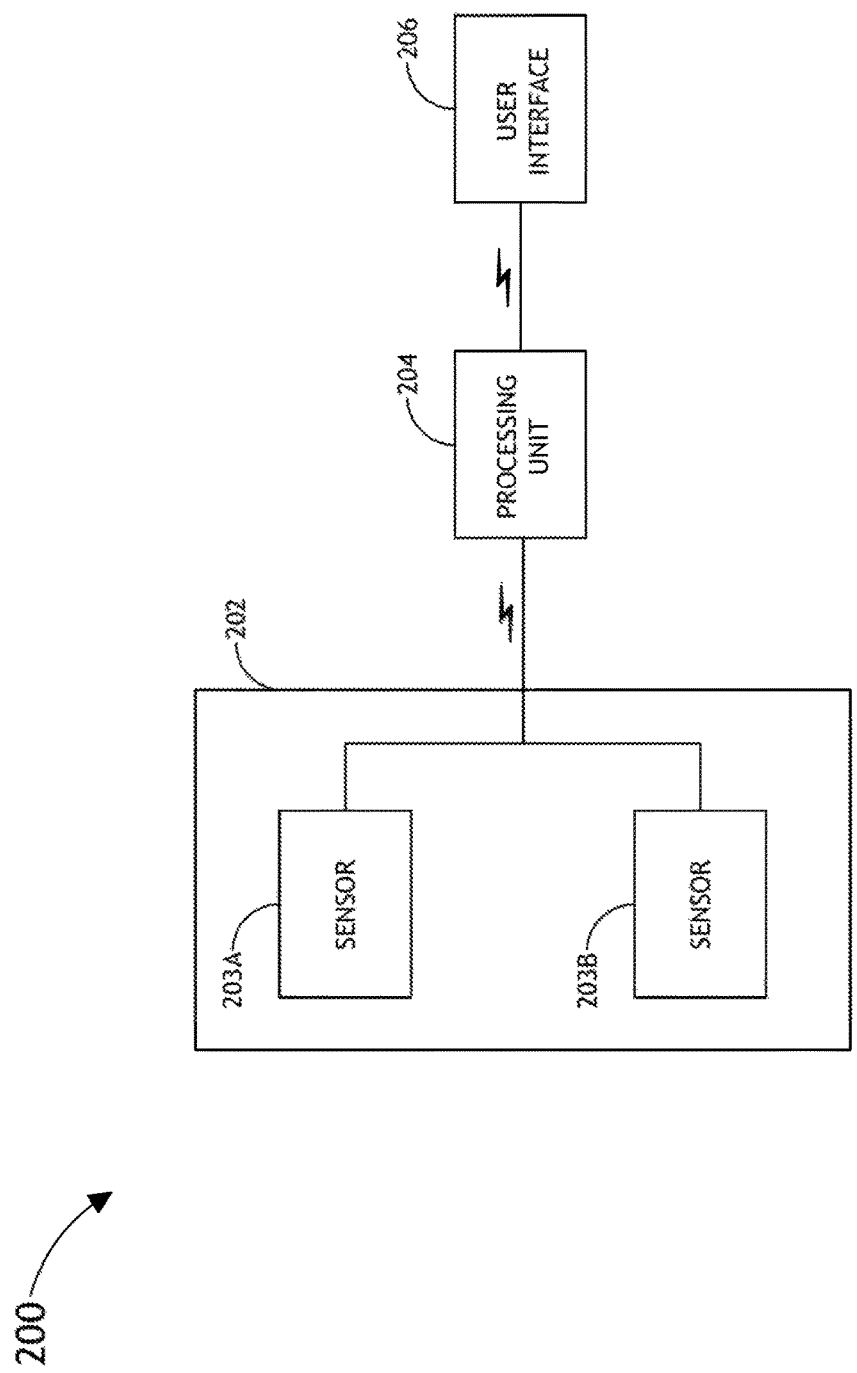
FIG. 2A is a block diagram illustrating a system for detecting and monitoring intrapleural air leaks utilizing fluid extracted from a pleural cavity of a patient, in accordance with an embodiment of this disclosure.

FIG. 2A illustrates a system 200 for detecting and monitoring air leaks utilizing fluid extracted from the pleural cavity by system 100 or any other chest drainage system known to the art. The system 200 includes at least one detection unit 202 configured to detect a presence of carbon dioxide and/or a second substance in an extracted portion of the pleural fluid. In some embodiments, the detection unit 202 includes at least a first sensor 203A configured to detect carbon dioxide and a second sensor 203B configured to detect the second substance. The second substance may include a non-toxically inhalable substance that is foreign to the human body such as, but not limited to, helium, sulfur hexafluoride, or nitric oxide. In some embodiments, a composition including the second substance, such as FDA approved HELIOX (79% helium, 21% oxygen), is presented to the patient for inhalation.

In some embodiments, the one or more sensors 203 of the detection unit 202 include diffusion based, spectral based, and/or thermal conductivity based sensors, operating either in a flow through or discrete mode. The detection/monitoring system 200 may include a single-sensor or multi-sensor configuration. In some embodiments, multiple sensors operating as a multi-modal system are contained in one detection unit 202. Exemplary sensors that may be at least partially incorporated into the detection unit 202 include, but are not limited to, carbon dioxide and helium analyzer sensors made by C-SQUARED INCORPORATED, or the VAISALA GM70 CO2 hand-held carbon dioxide meter produced by VAISALA, or the TEKNOKEOMA helium detector (Model #GL-2702-1941), or the helium leak detector produced by MARKES INTERNATIONAL LTD. The foregoing sensors are included for illustrative purposes only. The detection unit 202 may include any sensor or combination of sensors configured for quantitatively determining fluid concentration of carbon dioxide and the second substance to enable objective assessment of an intrapleural air leak.

In some embodiments, the one or more sensors 203 may further include a humidity sensor configured to detect a level of humidity or changes in the level of humidity at one or more locations along the drainage path or within the drainage canister 106. The changes in humidity may correlate to status (e.g. severity or recovery stage) of an air leak. Accordingly, the humidity sensor may enable an alternative method of air leak detection or may be configured to aid concentration sensors for improved air leak detection and/or quantification.

Detection of carbon dioxide in the pleural fluid is an initial indicator that an air leak exists. However, there are instances where carbon dioxide may be detected as a result of an air leak that has already healed. In addition, the inventors have determined that carbon dioxide detection with great precision (e.g. detecting a change in carbon dioxide concentration caused by a patient coughing) may be required to confirm the existence of an air leak. Accordingly, detection of the second substance allows for improved detection or confirmation of an existing air leak. Furthermore, by introducing a substance that is foreign to the human body, any detection of the foreign substance in the pleural fluid will accurately indicate the presence of an air leak.

The system 200 further includes at least one processing unit 204 in communication with the one or more sensors 203 of the detection unit 202. The processing unit 204 may include any combination of hardware, software, and/or firmware configured to perform one or more of the processing functions or steps described herein. In some embodiments, the processing unit 204 includes a computing system defined by a single or multiple core processor configured to execute program instructions from a carrier medium. The processing unit 204 may alternatively or additionally include a micro-controller, ASIC, FPGA, and/or a combination of logic gates and discrete components defining an electronic circuit.

The processing unit 204 is configured to collect information (e.g. Boolean values or measurements) from the one or more sensors 203 of the detection unit 202 indicating detection of carbon dioxide and/or the second substance. In some embodiments, the processing unit 204 is further configured to provide at least a first electrical signal when carbon dioxide is detected and a second electrical signal when the second substance is detected. A user interface 206 in communication with the processing unit 204 may be configured to provide visual and/or audible indications upon receiving the first signal and/or the second signal. The user interface 206 may include one or more audible or visual indicators such as, but not limited to, speakers, illumination sources, or a display unit (e.g. LED, LCD, or CRT display).

In some embodiments, the processing unit 204 is further configured to collect quantitative information (e.g. volume or percentage measurements) associated with a concentration of carbon dioxide and/or the second substance detected by the one or more sensors 203 of the detection unit 202. The processing unit 204 may be further configured to collect temporally successive measurements so that changes in the detected concentration of carbon dioxide can be monitored over a period of time. The user interface 206 may be further configured to display information associated with the measurements so that the status or rate of an air leak can be observed and tissue recovery can be assessed accordingly.

As illustrated in FIG. 1, the one or more sensors 203 of the detection/monitoring system 200 may be configured to receive a portion of the extracted pleural fluid through a three way adapter 208 fluidically coupled to the chest tube 102. It may be advantageous to detect for carbon dioxide and/or the second substance utilizing pleural fluid from the drainage path to avoid errors due to chemical or physical alteration which may result after disposition within the drainage canister 106. In some embodiments, the one or more sensors 203 are configured to receive a gaseous portion of the pleural fluid. For example, the adapter 208 may divert a gaseous portion of the fluid to the one or more sensors 203 or the one or more sensors may be disposed within a detection chamber when a liquid portion of the fluid is no longer flowing or has substantially ceased to flow along the drainage path.

Alternatively, the detection/monitoring system 200 may be disposed within the drainage canister 106 or fluidically coupled to an auxiliary port of the drainage canister 106. For example, the detection/monitoring system 200 may be configured to receive a portion of the extracted pleural fluid through a suction port 107 that is configured for interfacing with the pump 108. In some embodiments, the detection/monitoring system 200 may be directly coupled to the suction port 107 (when the pump 108 is removed) or the adapter 208 may be disposed along the suction path leading to the pump 108. There are several mechanisms by which the detection/monitoring system 200 may receive pleural fluid. However, the adapter 208 may advantageously allow the air leak detection/monitoring system 200 to interface with any chest drainage system, such as system 100, without significant interference. FIGS. 2B through 2E illustrate various embodiments of the adapter 208.

Figure 2B:
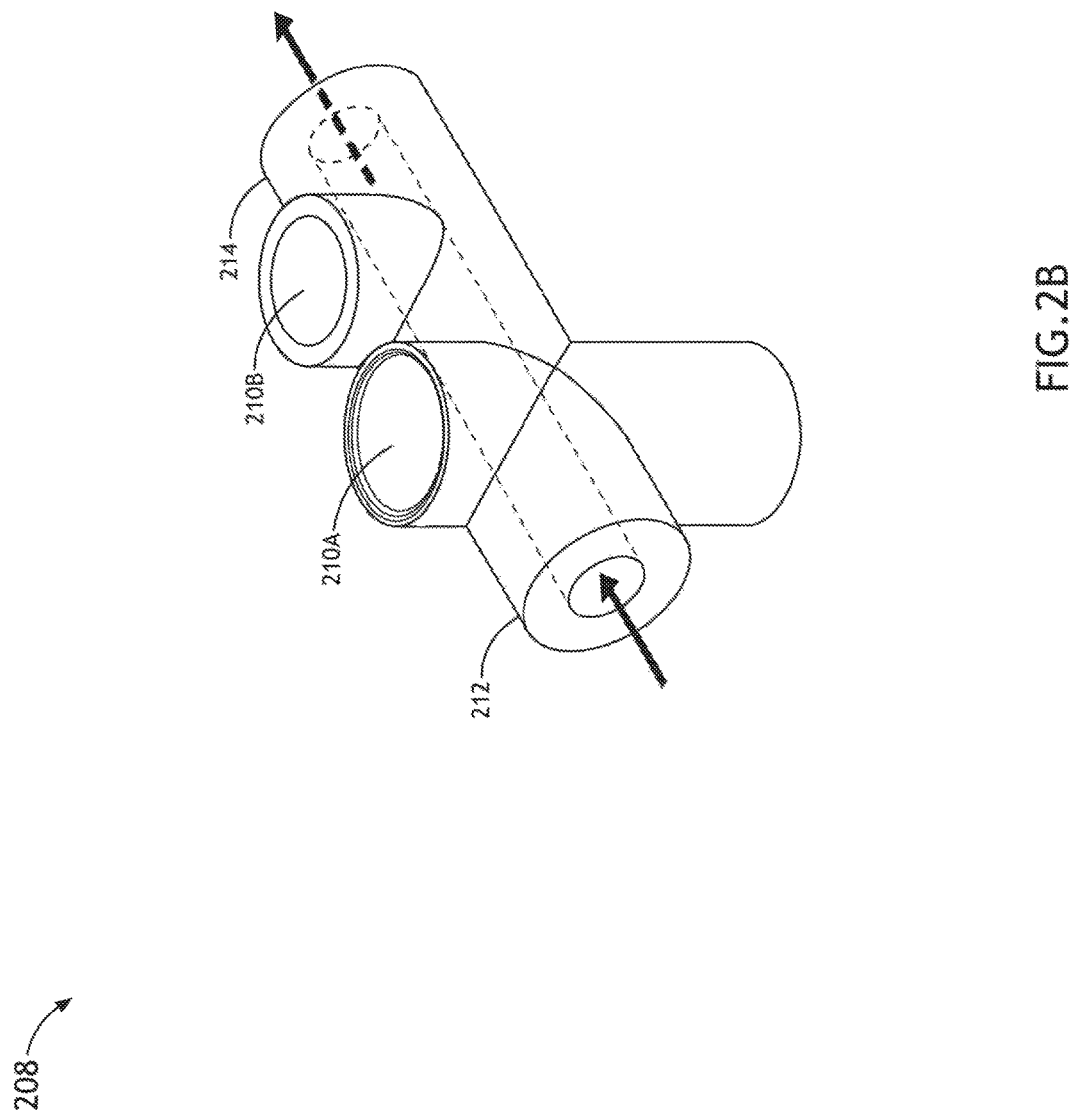
FIG. 2B illustrates a three way adapter for directing a portion of pleural fluid received from a chest tube along a detection path to at least one detection unit, in accordance with an embodiment of this disclosure.

As shown in FIG. 2B, the adapter 208 includes an inflow port 212 configured to receive extracted fluid from the chest tube 102 and an outflow port 214 configured to direct at least a portion of the fluid along a drainage path to the drainage canister 106. The adapter 208 further includes at least one port 210 configured for interfacing with the detection unit 202. In some embodiments, the adapter includes a first interface port 210A configured to receive a first sensor 203A and a second interface port 210B configured to receive a second sensor 203B. In some embodiments, the one or more sensors 203 of the detection unit 202 are configured to receive a gaseous portion of the fluid when a liquid portion of the fluid is no longer flowing through the adapter 208.

Figure 2C:
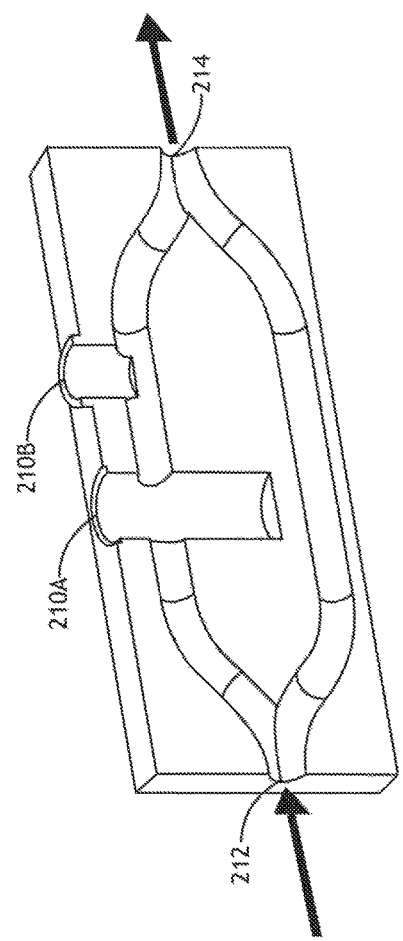
FIG. 2C illustrates the three way adapter, in accordance with another embodiment of this disclosure.

FIG. 2C illustrates another embodiment of the adapter 208 allowing a liquid portion of the fluid to flow through the adapter while the one or more sensors 203 of the detection unit 202 are inserted. The adapter 208 may be configured to channel fluid through a first (direct) path between the inflow port 212 and the outflow port 214 until liquid flow ceases and only gas flow remains. The adapter 208 may include one or more valves configured to close off the direct path allowing the gaseous portion of the fluid to flow through a second (sensing) path to the one or more sensors 203 via the one or more interface ports 210 of the adapter 208.

Figure 2D:
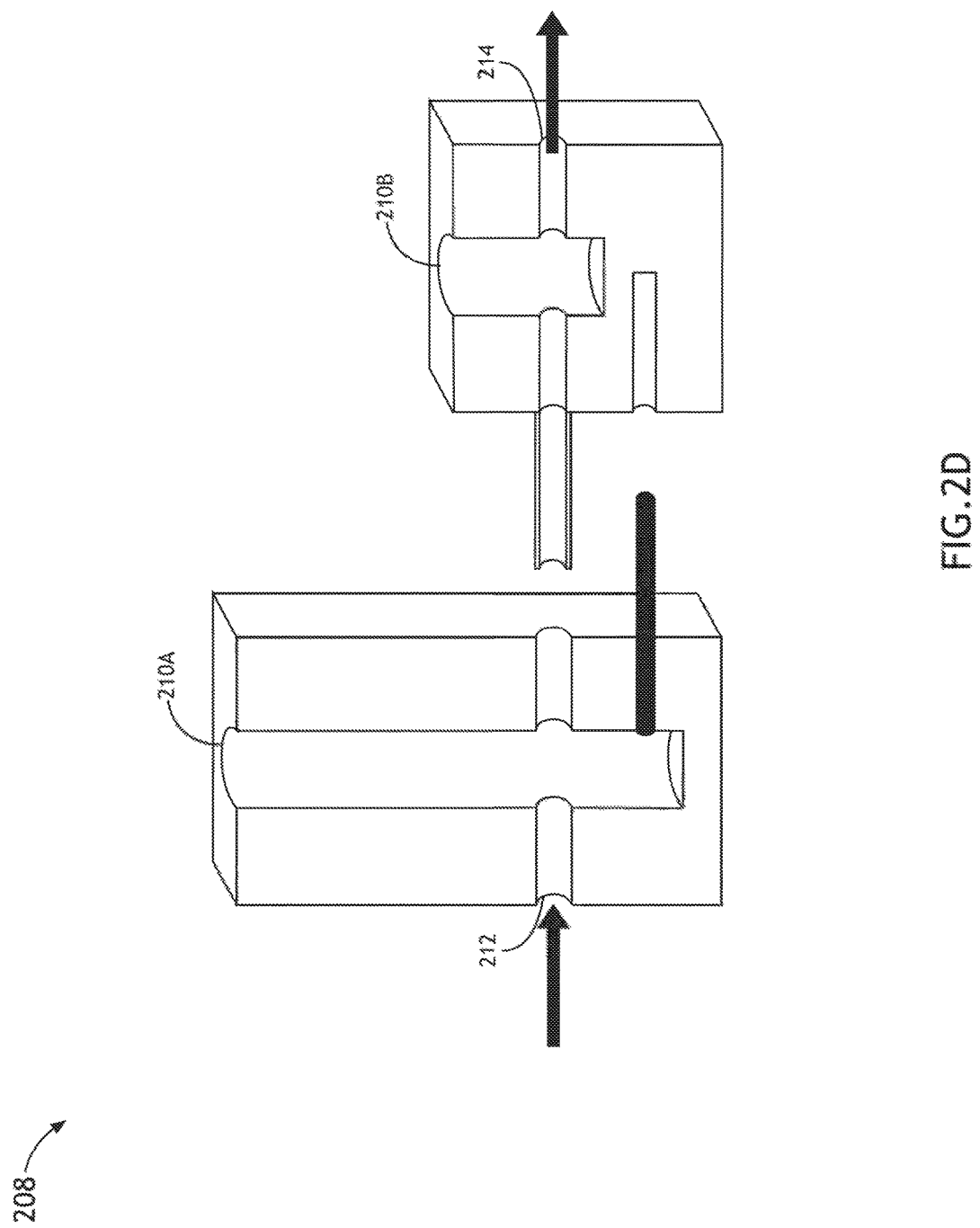
FIG. 2D illustrates the three way adapter, in accordance with another embodiment of this disclosure.

In another embodiment, illustrated in FIG. 2D, the adapter 208 includes two interlocking structures configured to slide in and out of one another. When liquid is flowing through adapter 208 the blocks are configured to slide together so that sensors are closed off from atmospheric air. The blocks are configured to be pulled apart when only gas flow is present to allow insertion of the first (carbon dioxide) sensor 203A into the first interface port 210A. A septum covering the second interface port 210B prevents exposure to atmospheric air when the second (second substance) sensor 203B is not in place. The second sensor 203B may be configured to receive a gaseous portion of the fluid through a needle inserted through the septum of the second interface port 210B.

Figure 2E:
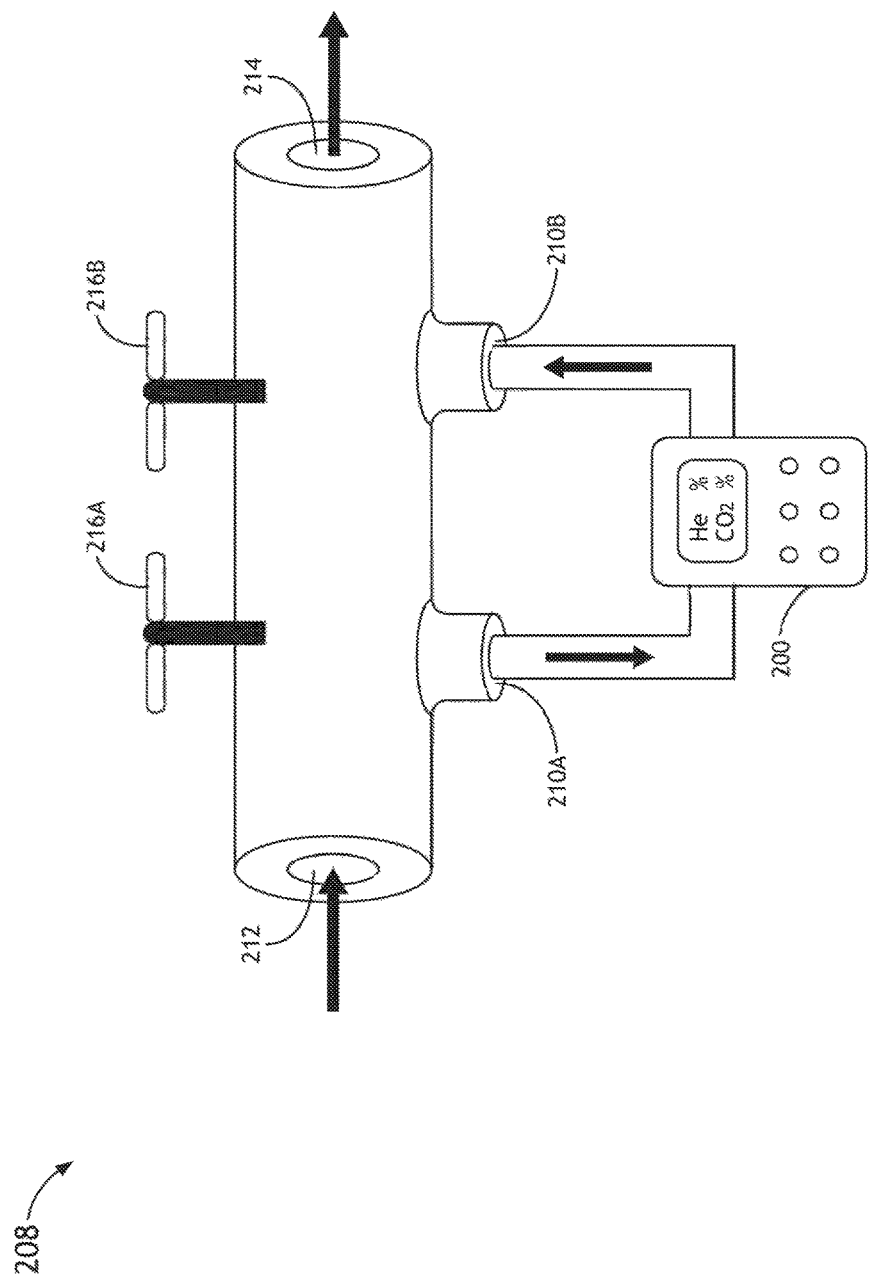
FIG. 2E illustrates the three way adapter, in accordance with another embodiment of this disclosure.

FIG. 2E illustrates yet another embodiment of the adapter 208 including two fluidically coupled three way valves. The valves are configured to allow pleural fluid to flow through the adapter from the inflow port 212 to the outflow port 214 under normal operation (i.e. chest drainage). The valves are further configured to divert a gaseous portion of the pleural fluid to the one or more sensors 203 of the detection unit 202 when the valves are actuated to a selected position. In some embodiments, the valves are mechanically actuated by turning one or more mechanically coupled gears or knobs 216 or by pulling or pushing a mechanically coupled shaft. In other embodiments, the valves may be pneumatically or electromagnetically actuated. When the adapter 208 is configured for detection by actuating the valves to the selected position, the gaseous portion moving through the adapter 208 may flow through a first interface port 210A to the detection unit 202 of system 200. The gas may be further directed from the system 200 back into the adapter 208 through a second interface port 210B and passed along a remainder of the drainage path (or suction path).

The adapter 208 may further include structural and/or mechanical features beyond those illustrated by the foregoing embodiments. The adapter 208 is intended to encompass any three way adapter known to the art. In some embodiments, the adapter 208 is further configured to be a "single-use" adapter. Accordingly, the adapter 208 may be constructed from disposable (pre-sterilized) plastic, rubber, and/or metallic materials. In other embodiments, the adapter 208 may be constructed from autoclavable or otherwise sterilizable materials. Furthermore, some or all of the connection ports and tubing utilizing for fluidically coupling the system 200 to the adapter 208 may be configured for removably attaching to one another. For example, the interface ports 210 may include tapered male connectors configured to receive tubing of the detection path. In some embodiments, the interface ports 210 may alternatively be cooperatively threaded or configured for mechanically fastening to the detection path tubing.

As further illustrated in FIG. 2E, the detection/monitoring system 200 may be configured for portable use. An enclosure made of lightweight materials (e.g. plastic and/or aluminum) may be configured to support or contain some or all of the detection unit 202, processing unit 204, and user interface 206 of the system 200. In some embodiments, the system 200 further includes a battery or power cell configured to supply power to the detection unit 202, processing unit 204, and user interface 206. In other embodiments, the system 200 may be configured to receive power through an electrical jack or adapter port. However, enabling the system 200 to be utilized without a power cord protruding from a wall outlet or generator may improve portability and provide sanitary advantages.

Figure 3:
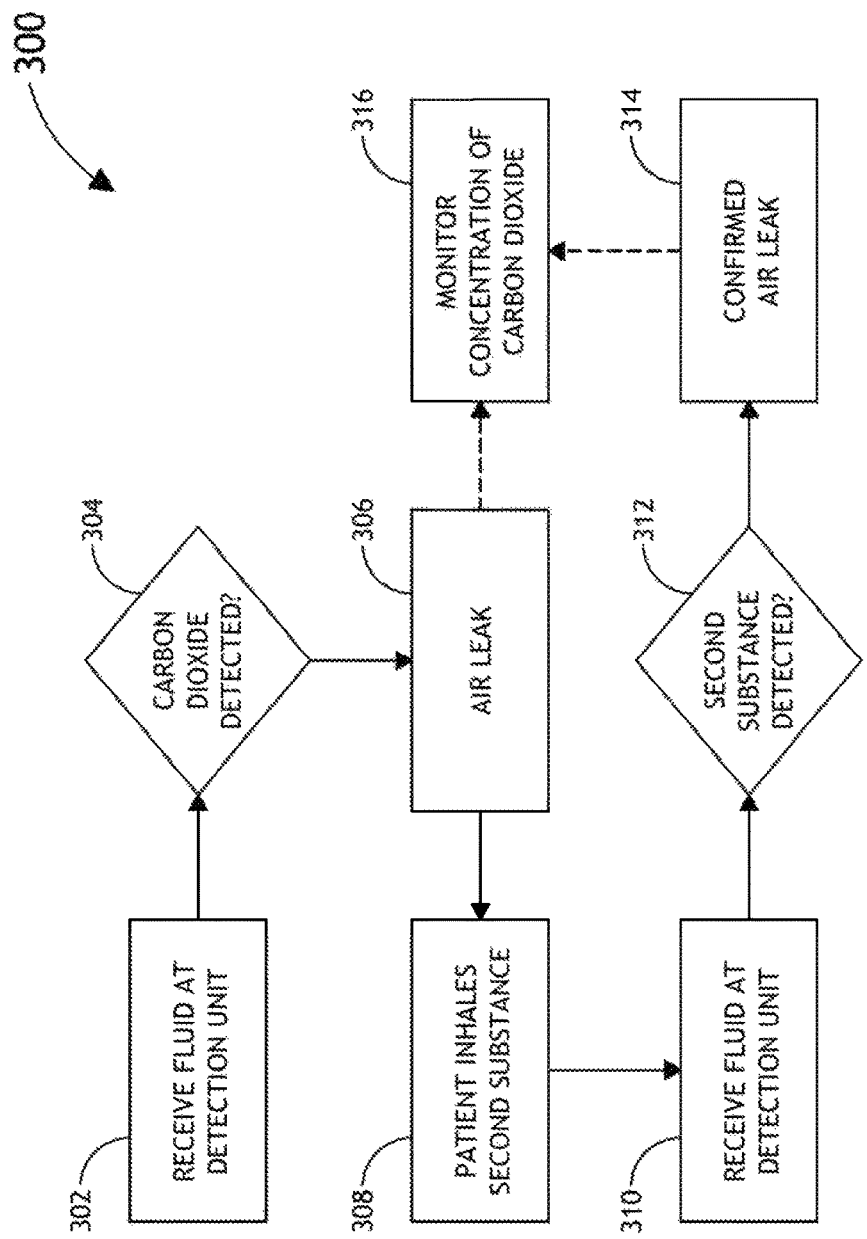
FIG. 3 is a flow diagram illustrating method of detecting and monitoring intrapleural air leaks, in accordance with an embodiment of this disclosure.

FIG. 3 is a flow diagram illustrating an embodiment of a method 300 for detecting and monitoring intrapleural air leaks. Systems 100 and 200 are manifestations of method 300 and all steps or features described with regard to embodiments of systems 100 and 200 may apply to method 300. However, it is noted herein that one or more steps of method 300 may be executed via means known to the art beyond those described with regard to systems 100 and 200.

At step 302, fluid is extracted from a pleural cavity of a patient utilizing a chest tube 102 or functionally equivalent device. At least a portion of the fluid, such as a gaseous portion of the fluid, is received by a carbon dioxide sensor. At step 304, the carbon dioxide sensor may detect a presence of carbon dioxide in the pleural fluid. At step 306, an audible or visual indicator provides a first indication when carbon dioxide is detected. The first indication may notify a clinician that an air leak exists or previously existed.

At step 308, a second substance or a composition (e.g. HELIOX) including the second substance is provided for the patient to inhale. In some instances, a clinician may provide a selected dose of the second substance for the patient to inhale. The clinician may further request that the patient cough to induce abrupt exhalation and trigger any air leaks. At step 310, fluid is extracted from the pleural cavity of the patient after the second substance is inhaled. At least a portion of the pleural fluid is received by a sensor configured to detect the second substance. At steps 312-314, an audible or visual indicator provides a second indication when the second substance is detected. The second indication may confirm the existence of an air leak at the time the second substance was introduced, thereby enabling the clinician to distinguish between an existing air leak and one that has already healed.

In some embodiments, the method 300 further includes monitoring the concentration of carbon dioxide aggregated in the extracted pleural fluid to assess the severity of an air leak and/or monitor tissue recovery. At step 316, a plurality of temporally successive measurements may be collected utilizing the carbon dioxide sensor. The measurements are analyzed to determine a change in the concentration of carbon dioxide over a period of time. As an air leak persists carbon dioxide may continue to accumulate in the extracted fluid; however, the rate of accumulation will decrease as the tissue recovers. Accordingly, a clinician can determine severity of tissue damage and monitor patient recovery by observing changes in the detected concentration of carbon dioxide over time.

It should be recognized that the various steps and functions described throughout the present disclosure may be carried out by a single computing system or by multiple computing systems. The one or more computing systems may include, but are not limited to, a personal computing system, mainframe computing system, workstation, image computer, parallel processor, or any other device known in the art. In general, the term "computing system" may be broadly defined to encompass any device having one or more processors, which execute instructions from at least one carrier medium.

Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. Program instructions implementing methods such as those described herein may be transmitted over or stored on carrier media. A carrier medium may include a transmission medium such as a wire, cable, or wireless transmission link. The carrier medium may also include a storage medium such as a read-only memory, a random access memory, a magnetic or optical disk, or a magnetic tape.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

What is claimed is:

1. A system for monitoring pleural fluid, comprising:
    at least one detection unit configured to receive fluid from a pleural cavity of a patient, detect carbon dioxide present in the fluid, and detect a second substance present in the fluid;
    at least one processing unit in communication with the at least one detection unit, the at least one processing unit configured to provide a first electrical signal when the at least one detection unit detects carbon dioxide, and provide a second electrical signal when the at least one detection unit detects the second substance; and
    an adaptor fluidically coupled to a chest tube, the adaptor comprising a first path configured to direct a gaseous portion of fluid received from the chest tube along a detection path to the at least one detection unit, and a second path configured to direct at least a liquid portion of the fluid received from the chest tube along a drainage path to a fluidically coupled drainage canister.

2. The system of claim 1, wherein the at least one detection unit comprises a first sensor configured to detect carbon dioxide and a second sensor configured to detect the second substance.

3. The system of claim 2, wherein the at least one detection unit further comprises a third sensor configured to detect a level of humidity or changes in the level of humidity at one or more locations along the drainage path or within the drainage canister.

4. The system of claim 1, wherein the second substance is non-toxically inhalable by the patient.

5. The system of claim 4, wherein the second substance comprises at least one of helium, sulfur hexafluoride, and nitric oxide.

6. The system of claim 1, wherein the at least one processing unit is further configured to acquire a plurality of temporally successive measurements associated with concentrations of carbon dioxide detected by the at least one detection unit.

7. The system of claim 1, further comprising:
an indicator in communication with the at least one processing unit, the indicator configured to provide at least one of an audible indication and a visual indication when at least one of the first electrical signal and the second electrical signal is received from the at least one processing unit.

8. A system for monitoring pleural fluid, comprising:
at least one detection unit configured to receive fluid from a pleural cavity of a patient, detect carbon dioxide present in the fluid, and detect a second substance present in the fluid;
at least one processing unit in communication with the at least one detection unit, the at least one processing unit configured to provide a first electrical signal when the at least one detection unit detects carbon dioxide, and provide a second electrical signal when the at least one detection unit detects the second substance;
a user interface in communication with the at least one processing unit, the user interface configured to provide a first indication when the first signal is received from the at least one processing unit, and provide a second indication when the second signal is received from the at least one processing unit; and
an adaptor fluidically coupled to a chest tube, the adaptor comprising a first path configured to direct a gaseous portion of fluid received from the chest tube along a detection path to the at least one detection unit, and a second path configured to direct at least a liquid portion of the fluid received from the chest tube along a drainage path to a fluidically coupled drainage canister.

9. The system of claim 8, wherein the at least one detection unit comprises a first sensor configured to detect carbon dioxide and a second sensor configured to detect the second substance.

10. The system of claim 9, wherein the second substance comprises at least one of helium, sulfur hexafluoride, and nitric oxide.

11. The system of claim 9, wherein the at least one detection unit further comprises a third sensor configured to detect a level of humidity or changes in the level of humidity at one or more locations along the drainage path or within the drainage canister.

12. The system of claim 8, wherein the second substance is non-toxically inhalable by the patient.

13. The system of claim 8, wherein the at least one processing unit is further configured to acquire a plurality of temporally successive measurements associated with concentrations of carbon dioxide detected by the at least one detection unit, and the user interface is further configured to display information associated with the plurality of temporally successive measurements.

14. The system of claim 8, wherein
the drainage canister is configured to receive fluid extracted from the pleural cavity of the patient by the chest tube, wherein the at least one detection unit is disposed within the drainage canister.

15. A method of monitoring pleural fluid, the method comprising the steps of:
receiving fluid from a pleural cavity of a patient;
directing a gaseous portion of fluid received from the pleural cavity of the patient along a detection path to at least one detection unit; and directing at least a liquid portion of the fluid received from the pleural cavity along a drainage path to a drainage canister;
detecting carbon dioxide present in the fluid;
providing a first indication when carbon dioxide is detected in the fluid;
detecting a second substance present in the fluid; and
providing a second indication when the second substance is detected in the fluid.

16. The method of claim 15, further comprising:
providing the second substance for inhalation by the patient.

17. The method of claim 15, wherein the second substance comprises at least one of helium, sulfur hexafluoride, and nitric oxide.

18. The method of claim 15, further comprising:
detecting a concentration of carbon dioxide in the fluid; and monitoring a change in the detected concentration of carbon dioxide over a period of time.

19. The method of claim 15, further comprising:
directing fluid received from the pleural cavity of the patient along the drainage path to the drainage canister, wherein at least one detection unit is disposed within the drainage canister.

* * * * *